(12) United States Patent
Conrad (10) Patent No.: US 11,284,908 B2
(45) Date of Patent: Mar. 29, 2022

(54) ADJUSTABLE ACETABULAR REAMERS AND METHODS

(71) Applicant: Zimmer, Inc., Warsaw, IN (US)

(72) Inventor: Steven Conrad, Albion, IN (US)

(73) Assignee: Zimmer, Inc., Warsaw, IN (US)

( * ) Notice: Subject to any disclaimer, the term of this patent is extended or adjusted under 35 U.S.C. 154(b) by 138 days.

(21) Appl. No.: 16/746,038

(22) Filed: Jan. 17, 2020

(65) Prior Publication Data
US 2020/0237381 A1 Jul. 30, 2020

Related U.S. Application Data

(60) Provisional application No. 62/797,449, filed on Jan. 28, 2019.

(51) Int. Cl.
| | | |
|---|---|---|
| *A61B 17/16* | (2006.01) | |
| *A61F 2/46* | (2006.01) | |
| *A61B 17/17* | (2006.01) | |

(52) U.S. Cl.
CPC ...... *A61B 17/1642* (2013.01); *A61B 17/1622* (2013.01); *A61B 17/1628* (2013.01); *A61F 2/4603* (2013.01); *A61B 17/17* (2013.01); *A61B 2017/1602* (2013.01); *A61F 2/4609* (2013.01)

(58) Field of Classification Search
CPC . A61B 17/16; A61B 17/1617; A61B 17/1622; A61B 17/1628; A61B 17/1633; A61B 17/1659; A61B 17/1662; A61B 17/1664; A61B 17/1666; A61B 2017/1602
See application file for complete search history.

(56) References Cited

U.S. PATENT DOCUMENTS

| | | | | |
|---|---|---|---|---|
| 3,702,611 | A * | 11/1972 | Fishbein | A61B 17/1666 606/81 |
| 6,283,971 | B1 * | 9/2001 | Temeles | A61B 17/1666 606/79 |
| 8,454,609 | B2 * | 6/2013 | Petit | A61B 17/1666 606/81 |
| 8,945,183 | B2 * | 2/2015 | Altarac | A61B 17/861 606/249 |
| 9,241,720 | B2 * | 1/2016 | Forsell | A61F 2/4607 |
| 9,375,315 | B2 * | 6/2016 | Forsell | A61L 27/58 |
| 9,517,076 | B2 * | 12/2016 | Papenfuss | A61B 17/1668 |
| 10,016,205 | B2 * | 7/2018 | Sausen | A61B 17/1666 |
| 10,105,150 | B2 * | 10/2018 | Bourque | A61B 17/1714 |

(Continued)

*Primary Examiner* — Eric S Gibson
(74) *Attorney, Agent, or Firm* — Schwegman Lundberg & Woessner, P.A.

(57) ABSTRACT

Described herein are examples of adjustable orthopedic reamer heads and methods for preparing a bone to receive an implant. The adjustable reamer heads and methods can include changing a cutting characteristic such as the size of an adjustable reamer head. In an illustrative example of an adjustable reamer head, the reamer head can include a housing, an actuator and a plurality of cutting elements. The plurality of cutting elements can be retained by the housing and can be operably coupled to the actuator. The plurality of cutting elements can include a first size cutting element and a second size cutting element. When the actuator is actuated, the first size cutting element and the second size cutting element can move relative to one another to change from a first cutting size to a second cutting size.

25 Claims, 11 Drawing Sheets

(56) References Cited

U.S. PATENT DOCUMENTS

| | | | | |
|---|---|---|---|---|
| 2004/0208717 | A1* | 10/2004 | Greenhalgh | B23B 51/0045 408/224 |
| 2005/0240193 | A1* | 10/2005 | Layne | A61B 17/1671 606/80 |
| 2006/0025774 | A1* | 2/2006 | Fishbein | A61B 17/1666 606/81 |
| 2006/0217730 | A1* | 9/2006 | Termanini | A61B 17/1666 606/81 |
| 2006/0264958 | A1* | 11/2006 | Ezzedine | A61B 17/1666 606/81 |
| 2007/0016211 | A1* | 1/2007 | Botimer | A61B 17/1666 606/81 |
| 2007/0112435 | A1* | 5/2007 | Tarabishy | A61B 17/1666 623/23.19 |
| 2007/0123921 | A1* | 5/2007 | Ek | A61B 17/32002 606/167 |
| 2008/0221505 | A1* | 9/2008 | Betts | A61B 17/8825 604/22 |
| 2008/0275449 | A1* | 11/2008 | Sackett | A61B 17/1668 606/80 |
| 2009/0171359 | A1* | 7/2009 | Sterrett | A61B 17/1675 606/80 |
| 2010/0168751 | A1* | 7/2010 | Anderson | A61B 17/7071 606/82 |
| 2010/0286697 | A1* | 11/2010 | Petit | A61B 17/1666 606/81 |
| 2011/0202060 | A1* | 8/2011 | White | A61B 17/1666 606/80 |
| 2012/0109229 | A1* | 5/2012 | Forsell | A61B 17/8875 606/86 R |
| 2012/0116523 | A1* | 5/2012 | Forsell | A61B 18/04 623/18.11 |
| 2014/0276844 | A1* | 9/2014 | Bourque | A61B 17/1615 606/80 |
| 2017/0035443 | A1* | 2/2017 | Sausen | A61B 17/1666 |
| 2017/0354424 | A1* | 12/2017 | Khalili | A61B 17/1693 |
| 2019/0083110 | A1* | 3/2019 | Wozencroft | A61B 17/1617 |
| 2020/0237381 | A1* | 7/2020 | Conrad | A61B 17/1617 |

\* cited by examiner

FIG. 7

ADJUSTABLE ACETABULAR REAMERS AND METHODS

CLAIM OF PRIORITY

This application claims the benefit of U.S. Provisional Patent Application Ser. No. 62/797,449, filed on Jan. 28, 2019, the benefit of priority of which is claimed hereby, and which is incorporated by reference herein in its entirety.

TECHNICAL FIELD

This document pertains generally, but not by way of limitation, to orthopedic devices, and, more particularly, to reamer systems, heads and methods.

BACKGROUND

Bone degradation, disease and injury are a common occurrence that can be treated with surgical intervention using an orthopedic device such as an orthopedic implant. Orthopedic implants can be used, for example, to replace a joint or portion of joint, or to provide fixation to a fractured bone while it heals.

In order to implant an orthopedic device, such as a hip implant, the surgeon can prepare the bone surface by a process such as reaming. An example of an implant site that can be reamed includes an acetabulum of a hip bone.

Reaming can be accomplished using a reamer system including a reamer head having cutting elements thereon. The reamer head can be rotated to remove and shape the bone at the implant site. To provide rotation for the reaming process, the reamer head can be attached to a driver by a handle (e.g., an extension, a coupling, an interface).

To achieve the proper bone surface, a surgeon can use multiple reamer head sizes in sequence to obtain the desired size and fit for the implant. This typically involves the use of two reamer handles so that the scrub technicians can be removing the previously used reamer head size and replace it with a larger reamer head size while the surgeon is working with a duplicate handle and different sized reamer head. In other words, two reamer handles are used in an attempt not to slow down the surgeon's incremental reaming.

For example, when the surgeon is done reaming with a first reamer head (smallest size), the surgeon hands a first handle with the first reaming head back to the surgical technician, who then hands the surgeon a second handle with a second reamer head (larger size) assembled to the second handle. While the surgeon is reaming with the second reamer head, the surgical technician is replacing the first reamer head on the first handle with a third reamer head (larger than the second reamer head) to be ready to exchange again with the surgeon.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various examples discussed in the present document.

DETAILED DESCRIPTION

As discussed above, orthopedic implants can be secured to bone, for example, to replace a joint or portion of joint. To implant an orthopedic device, the surgeon can prepare the bone by removing bone material and shaping it to receive the implant.

In some hip replacement procedures, to remove and shape the bone, the surgeon can ream the bone surface using a driver that is adapted to interface with a reamer head. The reamer head can include cutting elements, that, when rotated by the driver, scrape the bone surface to remove bone and carry the bone away from the implant site.

To achieve the proper bone surface, a surgeon may need to utilize multiple reamer head sizes in sequence to obtain the desired size and fit for the implant. The result of this process is inefficient use of time and space in the operating room and the need for multiple reamer heads and handles.

The reamer systems, heads and methods described herein can reduce extra steps, motion and instruments in the operating room. Because of these reductions, the variation in surgical procedures from surgeon to surgeon can also be reduced. These benefits are obtained through the reamer systems and/or heads including a plurality of cutting elements configured in a selectable manner to enable incremental reaming using a single device.

The reamer systems, heads and methods described herein can also reduce the number of surgical instruments that need to be cleaned after the surgical procedure. By reducing the number of instruments needed to perform the surgical procedure, the number of instruments that need to be cleaned and sterilized is reduced. Consequently, using fewer instruments can also reduce cross-contamination between patients.

Figure 1:
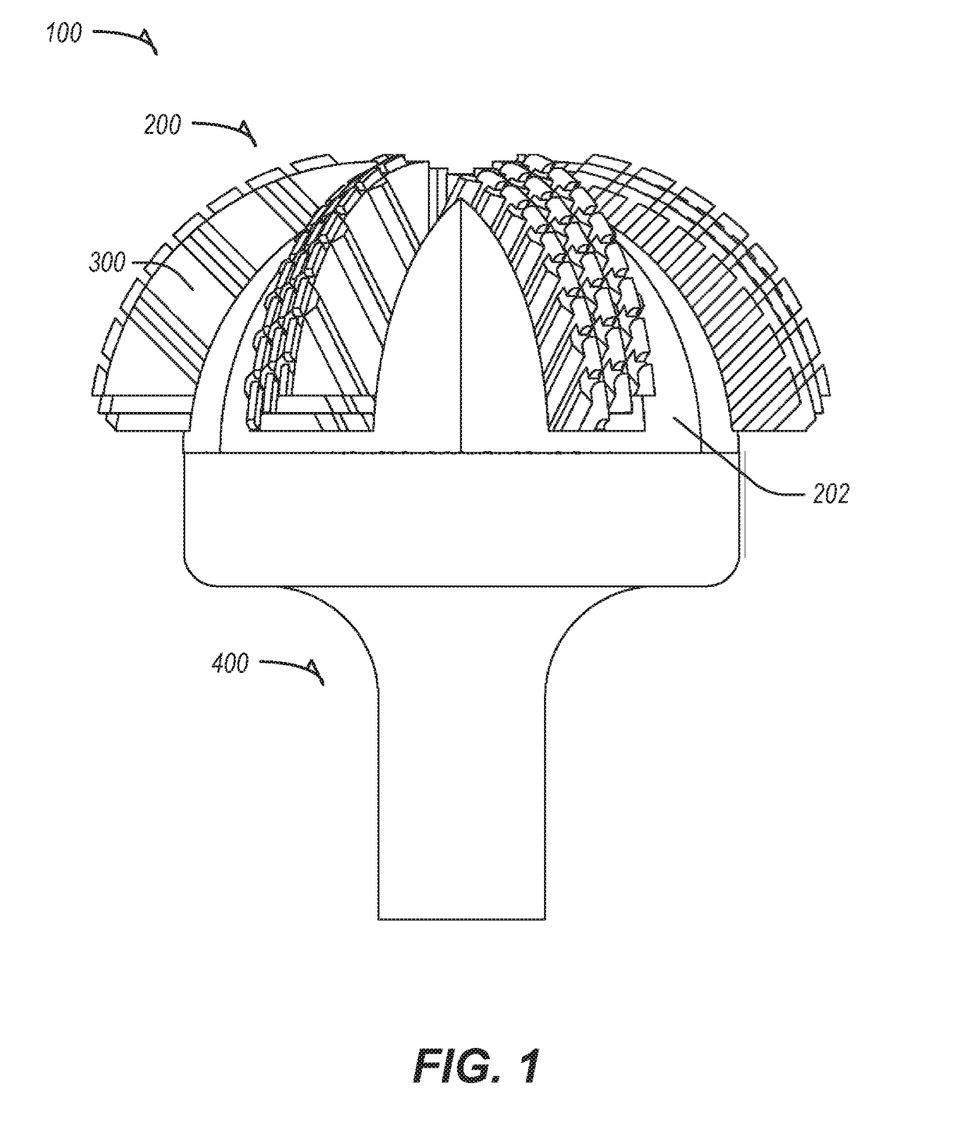
FIG. 1 is a side view of an illustrative orthopedic reamer system including a reamer head and a handle, in accordance with at least one example.

FIG. 1 illustrates a side view of an orthopedic reamer system 100 including a reamer head 200 and a handle 400, in accordance with at least one example. The reamer head 200 can include a housing 202 and a plurality of cutting elements 300 retained by the housing 202. The plurality of cutting elements 300 (hereinafter cutting elements) can be moved relative to one another to change the geometry of the reamer head 200 from a first cutting geometry to a second cutting geometry. In some examples, the change in cutting geometry can include a change is size, shape, or depth; or the amount of bone removed by the cutting elements 300.

The handle 400 can extend away from the reamer head 200. The handle 400 can provide the surgeon an interface to provide directional and pressure control while transferring rotational motion from a driver to the reamer head 200.

Figure 2A:
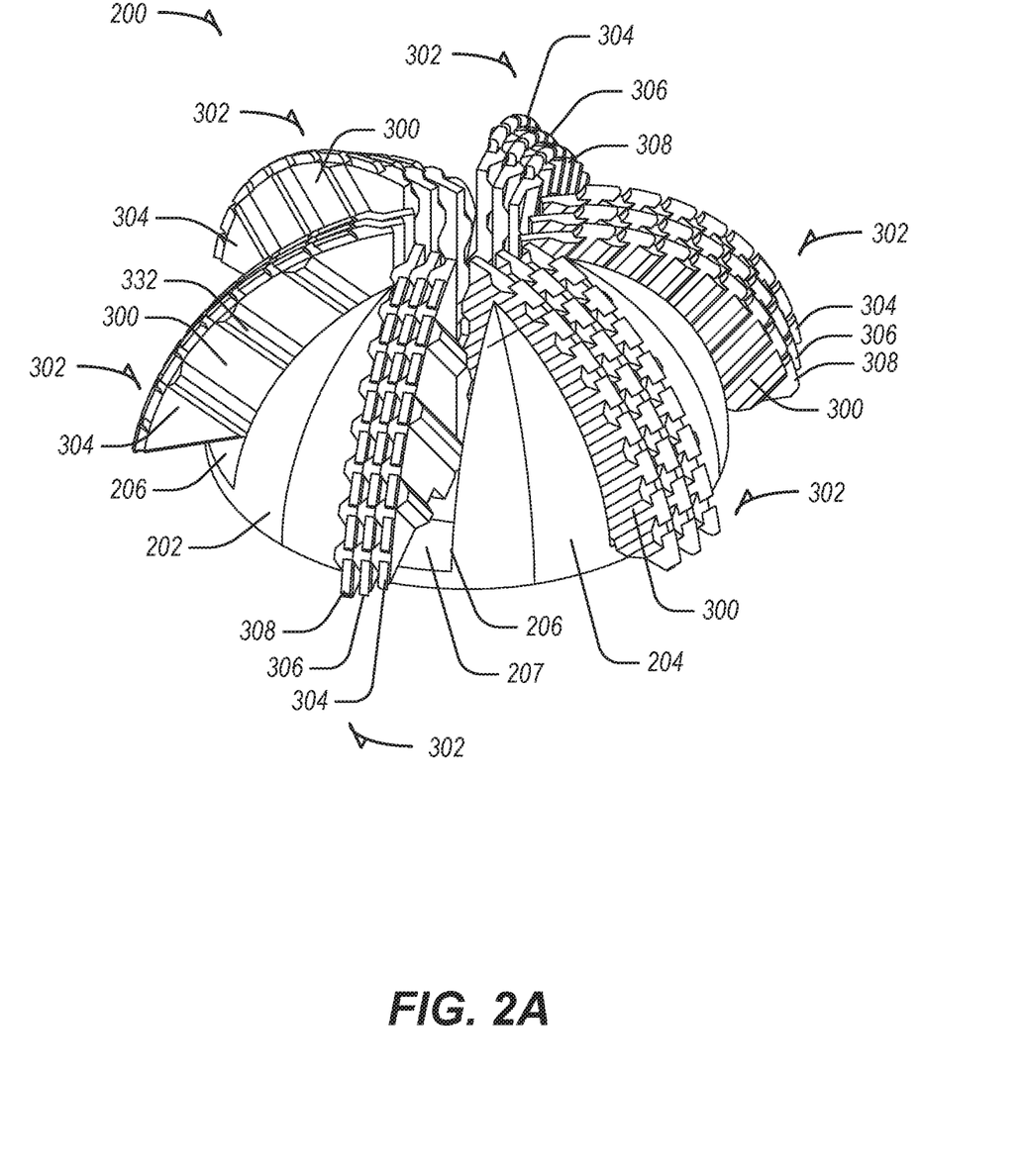
FIG. 2A is a top perspective view of the reamer head of FIG. 1, in accordance with at least one example.
Figure 2B:
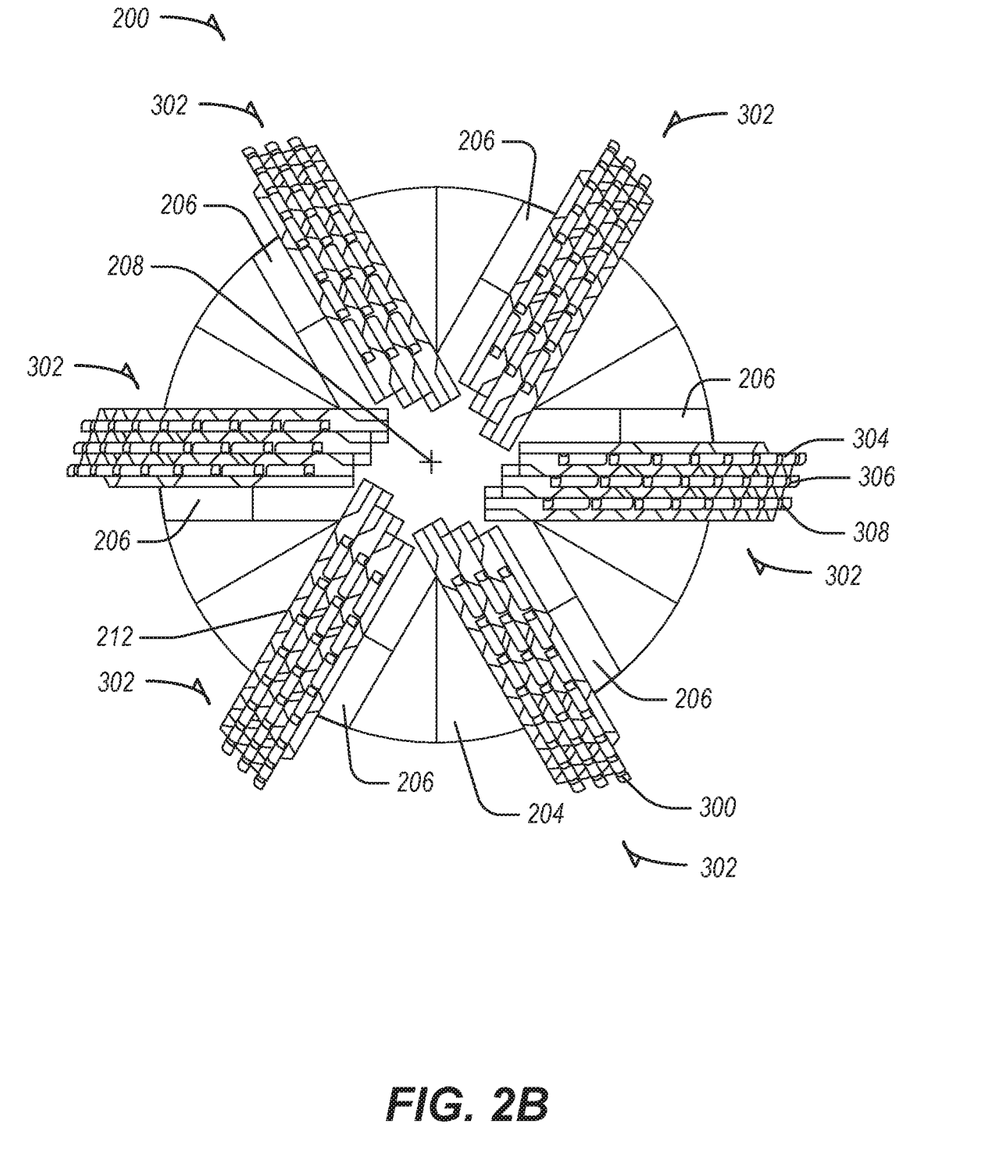
FIG. 2B is top view of the reamer head of FIG. 1, in accordance with at least one example.
Figure 2C:
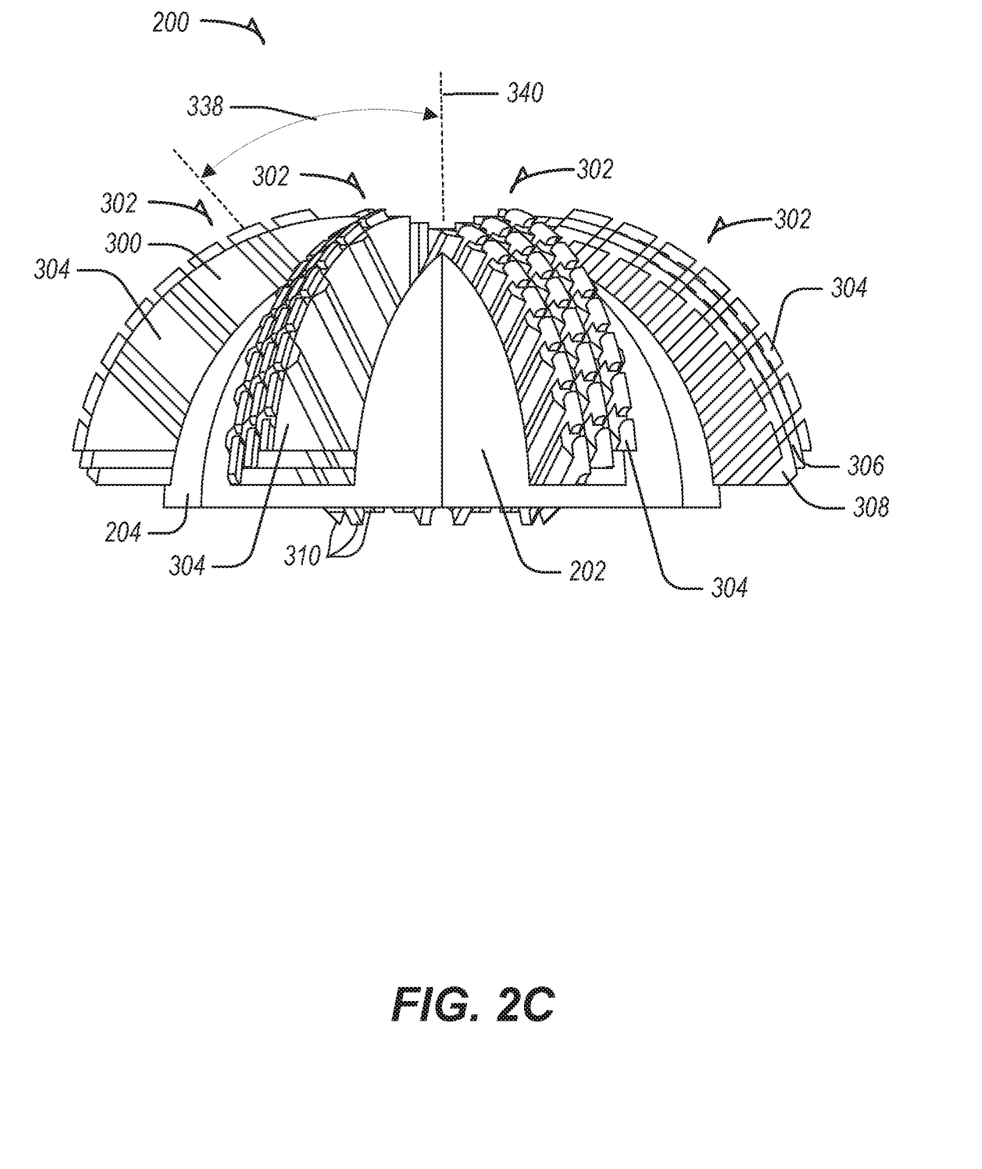
FIG. 2C is a side view of the reamer head of FIG. 1, in accordance with at least one example.

FIGS. 2A-2C show perspective, top and side views of the reamer head 200 of FIG. 1. The illustrative housing 202 can include a generally hemispherical shaped dome 204 having a plurality of slots 206 arranged in a generally starburst form (FIG. 2B). In the example, a total of six slots 206 intersecting at a center (208, FIG. 2B) of the housing 202 are shown, however any number of slots 206 (FIG. 2B) can be provided. The plurality of slots 206 (hereinafter slots) are shown intersecting each other proximate the center of the housing 202, or in other words, extending across the dome.

As shown in FIG. 2B, in some examples, the slots 206 may not extend across the entire dome 204 as shown, instead, each of the slots 206 can be separate and terminate before reaching the center 208 of the dome 204. In some examples, instead of the slots 206 having a linear form, each of the slots 206 can be curved so that the starburst form can extend outward from the center 208 in a curved shape, instead of the linear slot shape shown, to form a spiral starburst form. A spiral starburst form can be similar to the starburst form shown, but instead of each of the slots being linear, they can be curved, for example, in an arc shape, or a portion of a circle shape. Other slot shapes can be provided that include non-linear, discontinuous and angled portions.

The cutting elements 300 can extend outward (e.g., radially outward) from the slots 206. The housing 202 can retain the cutting elements 300 but still allow the cutting elements 300 to be movable relative to the housing 202. The cutting elements 300 can be movable relative to one another to change the cutting geometry of the reamer head 200.

The slots 206 can include a bone collecting region 207 (FIG. 2A) to collect bone that has been removed by the cutting elements 300. The collected bone can be removed from the implant site, and can be mixed with other materials (e.g., bone cement) and used by the surgeon to secure the implant to the bone tissue.

In the example of FIG. 2A-2C, six sets 302 of cutting elements 300 are shown, three in each slot 206. Each slot 206 can have a respective set 302 of cutting elements 300 including a first cutting element 304, a second cutting element 306 and a third cutting element 308. It can be beneficial to arrange and disperse the sets 302 of cutting elements 300 radially around the center 208 (FIG. 2B) of the housing 202. However, any number of sets 302 of cutting elements can be provided, including a single set 302 of cutting elements 300.

As shown in FIG. 2A and described in further detail with respect to FIGS. 3A-3D, the cutting elements 300 can include alignment elements 332. The alignment element 332 can engage with an alignment guide 212 in the housing 202, shown in FIG. 2B. In some examples, the alignment guide 212 can include a formation in the slot 206 (FIG. 2B) that complements the shape of the alignment elements 332. In this example, the alignment element(s) 332 have a truncated linear pyramid shape running along a length of the cutting element 300. The alignment elements 332 can run, for example, along an angle 338 (such as a 45 degree angle) relative to a center axis 340 of the housing (FIG. 2C). Locating the alignment elements 332 along the 45 degree angle as described allows each of the cutting elements 300 to move in a direction that provides a correct diametric location when the cutting element 300 is extended.

The cutting elements 300 are illustrated has having three to eight alignment elements 332. In certain examples, the cutting elements 300 can include alignment elements disposed on both sides, with adjacent cutting elements 300 including alignment elements 332 positioned to interleave between adjacent cutting elements 300 when the cutting elements 300 are positioned within a set 302 in a slot 206. In other examples, the alignment elements 332 can have different profiles, such as a semicircular profile or a rectangular profile. Cutting elements 300 and alignment elements 332 are discussed further below in reference to FIGS. 3A-3F.

Figure 4A:
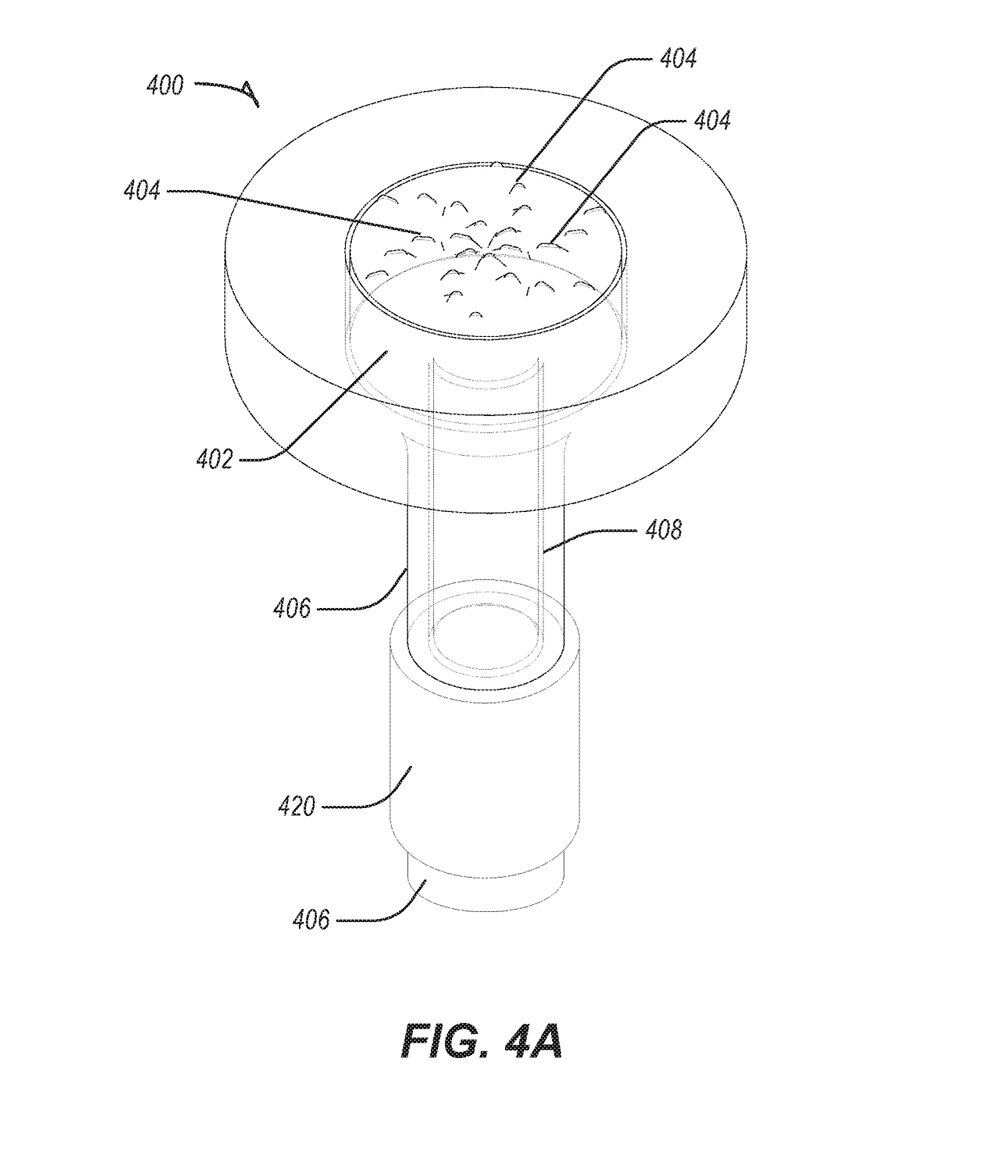
FIG. 4A shows a perspective view of an illustrative handle of the orthopedic reamer system of FIG. 1, in accordance with at least one example.
Figure 4B:
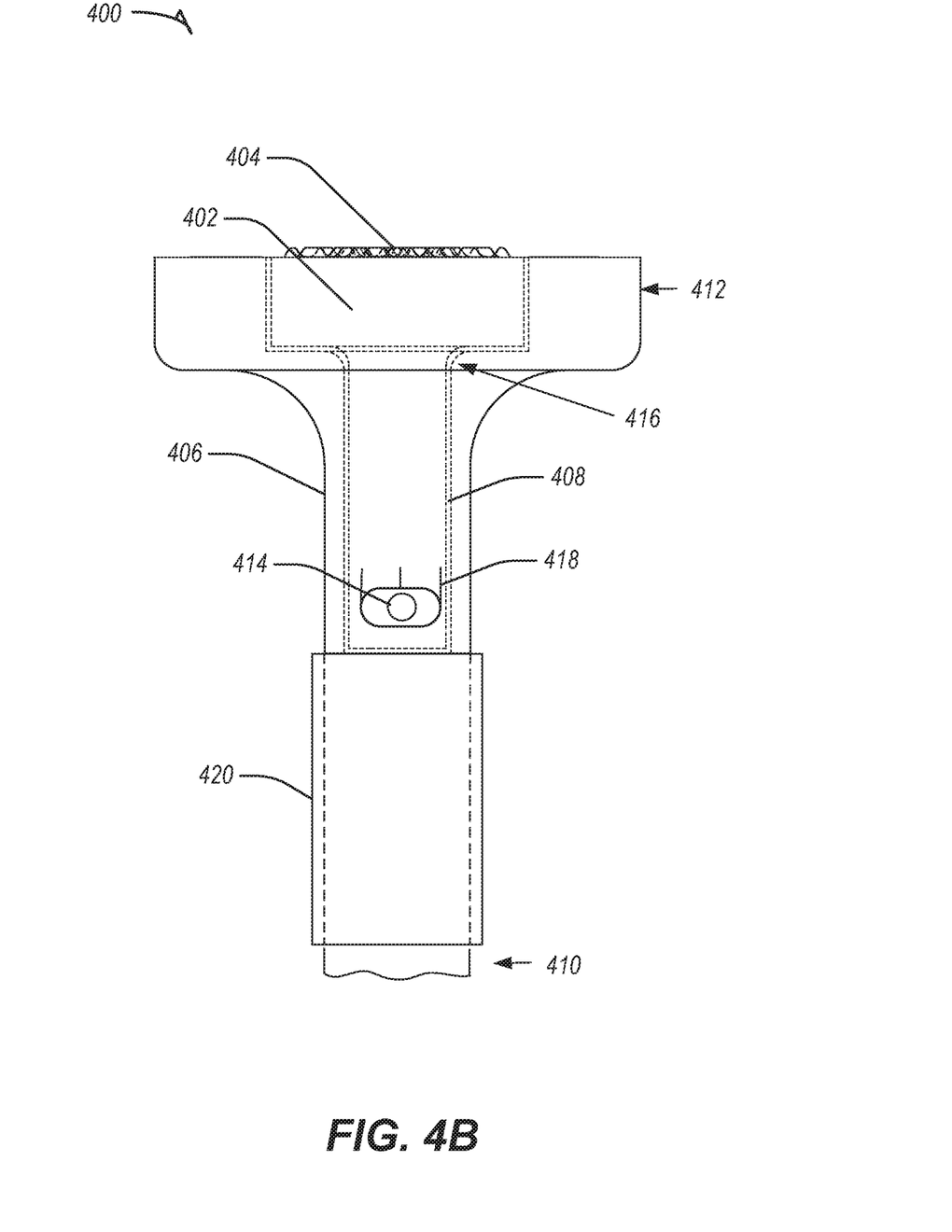
FIG. 4B shows a side view of the handle of the orthopedic reamer system of FIG. 1, in accordance with at least one example.

To change the cutting geometry of the reamer head, the cutting elements 300 can be operably coupled to an actuator 402 (FIG. 4A-4B). The actuator 402 can move the cutting elements 300 relative to the housing 202 and relative to each other to change the cutting geometry of the reamer head 200. In the illustrative example reaming system 100, the actuator 402 is provided on a handle 400 that is described in further detail in FIGS. 4A and 4B. In other examples, the actuator 402 can be disposed in the portion of the housing 202 that forms reaming head 200.

In some examples, changing the cutting geometry of the reamer head 200 includes changing the cutting size from a first size to a second size or a third size. For example, by changing which cutting element 304, 306, 308 is actuated (e.g., extended), the reamer head 200 can be adjusted from a 52 millimeter (mm) first size cut performed by the first cutting elements 304, to a 54 mm second size cut performed by the second cutting elements 306. Further, the reamer head 200 can be adjusted to a 56 mm third size cut performed by the third cutting elements 308. The first, second and third sizes are merely provided as an example. Any suitable size or shape can be provided to cover the range of reaming (e.g., cutting) sizes needed for a specified patient, or a specified population of patients.

In FIGS. 2A-2C, the first cutting elements 304 are shown in an extended position. When the first cutting elements 304 are in the extended position, the first cutting elements 304 are positioned to provide the cutting action of the reamer head 200. When the first cutting elements 304 are in the extended position, the second and third cutting elements 306, 308 can be in a retracted position and may not provide any cutting action.

In some examples, and as shown in FIG. 2C, the first cutting elements 304 can be the smallest cutting elements, the second cutting elements 306 can be larger than the first cutting elements 304, and the third cutting elements 308 can be the largest cutting elements. Any number of cutting elements 300 and any ordering of the sizes (e.g., largest to smallest, smallest to largest, or a non-successive order) can be provided. In some examples, the cutting elements 300 can skip sizes. In use, the surgeon may be able to skip sizes to best suit the surgeon or the surgical procedure. For example, the surgeon can ream the first size and then move directly from the first size to the third size.

FIG. 2C also shows actuation interfaces 310 on each of the cutting elements 300 that will be described in further detail in FIG. 3B. The actuation interfaces 310 can interact with displacement elements 404 on the actuator 402, shown in FIGS. 4A and 4B, to extend the first cutting elements 304, the second cutting elements 306 or the third cutting elements 308, depending on a rotation position of the actuator 402.

Figure 3A:
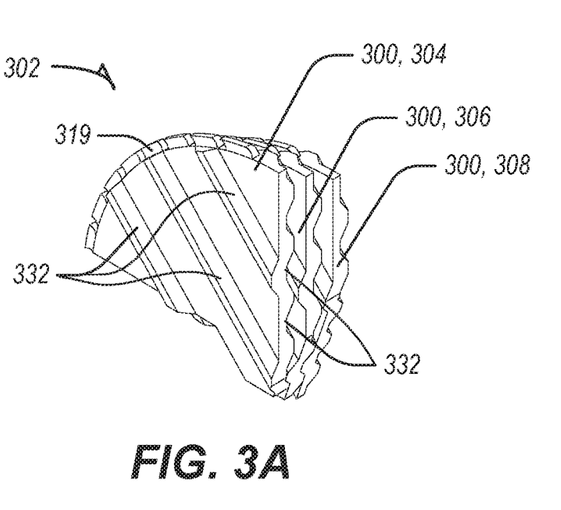
FIG. 3A is a perspective view of an illustrative set of cutting elements that can be used with the reamer head of FIG. 1, in accordance with at least one example.
Figure 3B:
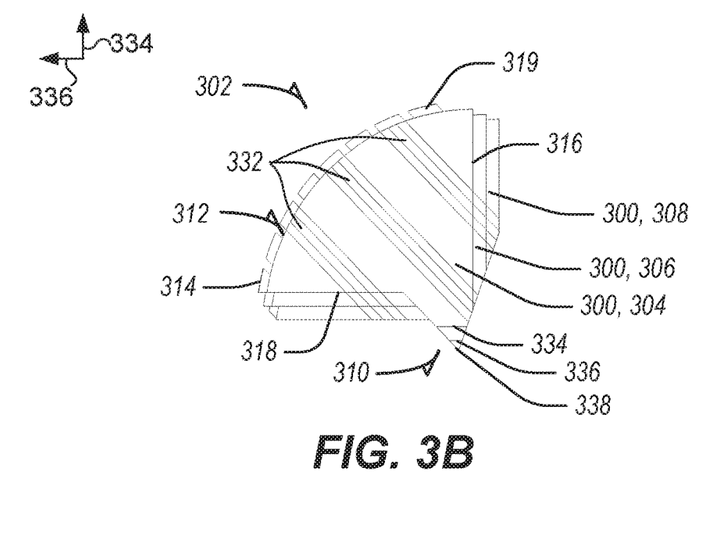
FIG. 3B is a side view of the set of cutting elements of FIG. 3A, in accordance with at least one example.
Figure 3C:
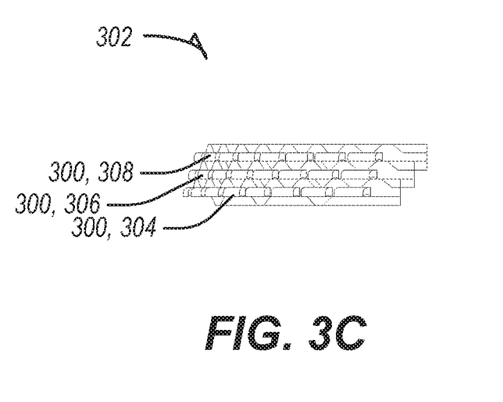
FIG. 3C is a top view of the set of cutting elements of FIG. 3A, in accordance with at least one example.
Figure 3D:
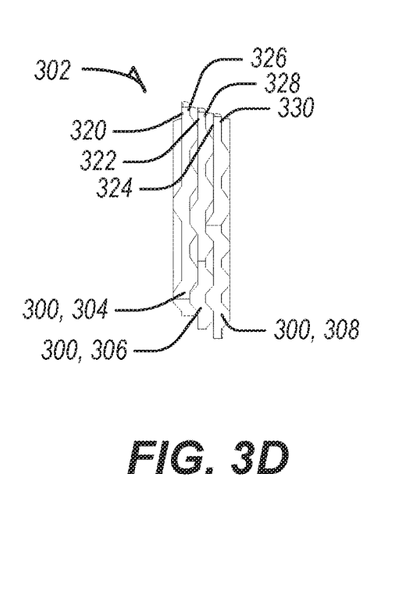
FIG. 3D is a view of the set of cutting elements of FIG. 3A from the center (see, FIG. 2B) of the reamer head facing radially outward towards the cutting elements, in accordance with at least one example.

FIGS. 3A-3D show different views of a set 302 of cutting elements 300 that can be used in the reamer head of FIGS. 1, 2A-2C. In particular, FIG. 3A shows a perspective view of one set 302 of cutting elements 300 (first, second and third cutting elements 304, 306, 308). FIGS. 3B-3C are top and side views of the set 302 of cutting elements 300 of FIG. 3A. FIG. 3D shows a view of the set 302 of cutting elements 300 looking from an inner edge 316 (see, FIG. 3B) facing radially outward.

Each of the first, second and third cutting elements 304, 306, 308 can have an outer perimeter 312 including edges (e.g., faces). For example, as labeled for the first cutting element 304, the outer perimeter 312 can include a cutting edge 314, the inner edge 316, and a proximal edge 318 extending from the cutting edge 314 to the inner edge 316. The cutting edge 314 can include a curved cutting portion having teeth 319 (FIGS. 3A and 3B). As described herein, teeth 319 can include any type of cutting implement including abrasive materials adapted for preparing a bone surface.

With reference to FIG. 3D, each of the first, second and third cutting elements 304, 306, 308 can also have a leading face 320, 322, 324 and a trailing face 326, 328, 330 opposite the leading face 320, 322, 324. The leading face 320, 322, 324 can be the surface of the cutting elements 300 that first comes into contact with the bone tissue during reaming, while the trailing face 326, 328, 330 follows behind during rotation.

Each of the leading face 320, 322, 324 and the trailing face 326, 328, 330 can include alignment elements 332 (FIGS. 3A and 3B) to align the cutting elements 300 with each other and with the housing 200 (FIG. 2A). The alignment elements 332 can be linear in form. In some examples, the alignment elements 332 can be non-linear or include both linear and non-linear, or discontinuous portions. Although a plurality of alignment elements 332 are shown on each cutting element 300, in some examples, a single alignment element 332 can be provided.

As shown in FIGS. 3A and 3B, the alignment elements 332 can be raised or recessed portions (e.g., ridges, grooves) that serve to align one of the cutting elements 300 (e.g., 304) with complementary alignment elements 332 on an adjacent cutting element 300 (e.g., 306).

With reference to FIG. 3B, the alignment elements 332 can provide alignment in a longitudinal direction 334, an axial direction 336, or a combination of both the longitudinal 334 and axial 336 directions as shown. In the example, the alignment elements 332 are arranged linearly on a diagonal to provide alignment having a combined longitudinal direction 334 component and an axial direction 336 component. The housing 200 can have a complementary alignment guide 212 to control the alignment of the set 302 of cutting elements 300 with respect to the housing 200 (FIG. 2B). In some examples, the alignment guide 212 can be located in the slot 206 (FIG. 2B).

The first cutting element 304, the second cutting element 306, and the third cutting element 308 can be nested together to allow the first, second and third cutting elements 304, 306, 308 to translate relative to each other along the direction of the alignment elements 332.

Together, FIGS. 3E-3J show perspective and side views of the set 302 of cutting elements 300 of FIGS. 3A-3D in three different cutting positions.

Figure 3E:
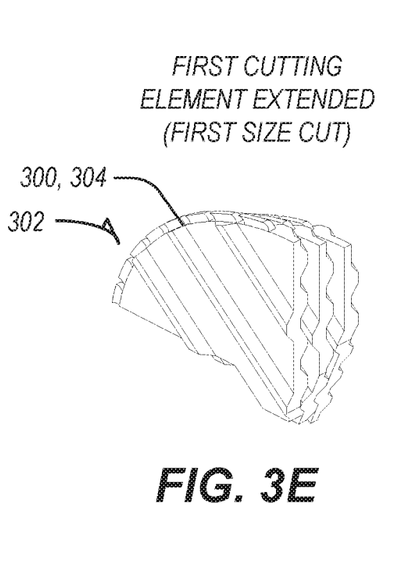
FIGS. 3E and 3F are perspective and side views of the set of cutting elements of FIG. 3A, arranged (e.g., actuated) to ream a first size, in accordance with at least one example.
Figure 3F:
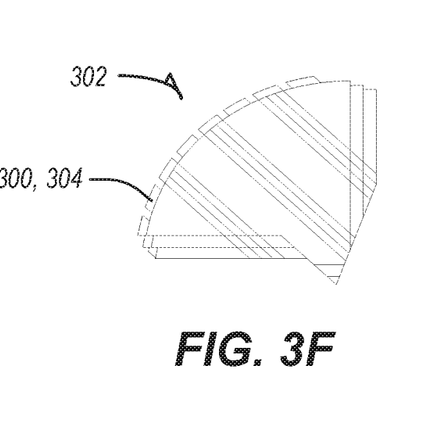

FIGS. 3E and 3F show the set 302 of cutting elements 300 actuated to ream a first size with the first cutting element 304 in an extended position. The first cutting element size can, for example, approximate or be equivalent to a 52 mm sized reamer head (e.g., 52 mm radius).

Figure 3G:
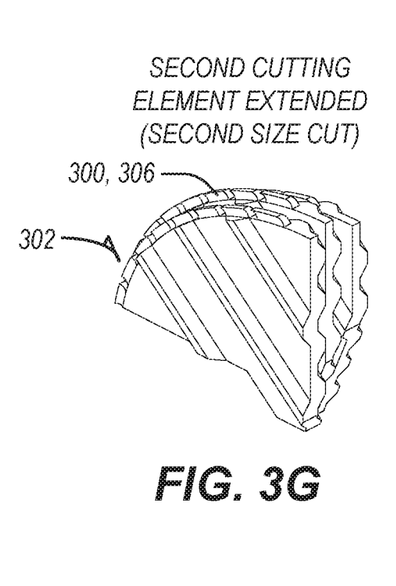
FIGS. 3G and 3H are perspective and side views of the set of cutting elements of FIG. 3A, arranged (e.g., actuated) to ream a second size, in accordance with at least one example.
Figure 3H:
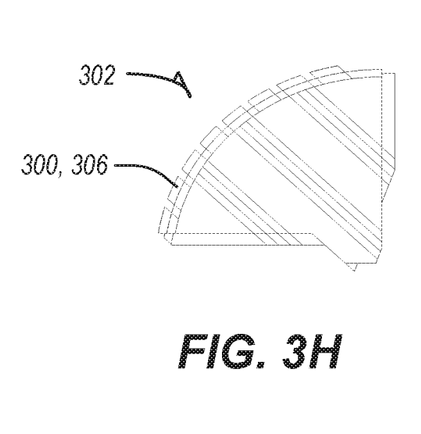

FIGS. 3G and 3H show the set 302 of cutting elements 300 of FIG. 3A actuated to ream a second size with the second cutting element 306 in an extended position. The second cutting element size can, for example, approximate or be equivalent to a 54 mm sized reamer head.

Figure 3I:
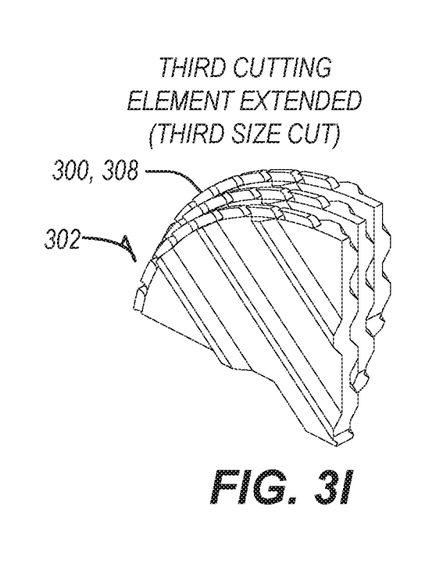
FIGS. 3I and 3J are perspective and side view of the set of cutting elements of FIG. 3A arranged (e.g., actuated) to ream a third size, in accordance with at least one example.
Figure 3J:
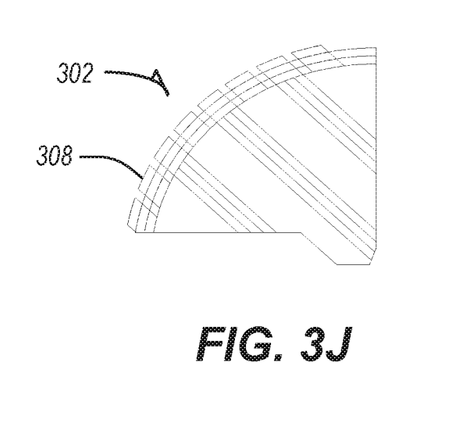

FIGS. 3I and 3J show the set 302 of cutting elements 300 actuated to ream a third size with the third cutting element 308 in an extended position. The third cutting element size can, for example approximate or be equivalent to a 56 mm size reamer head.

In some examples, rather than, or in addition to changing size, other aspects of the geometry can be varied between the first, second and third cutting elements. For example, the depth, roughness or shape, among other features, can be different between the first, second and third cutting elements to prepare the bone to receive an implant.

FIGS. 4A and 4B show perspective and side views of a handle 400 of the reamer system 100 of FIG. 1, in accordance with at least one example. The handle 400 can be adapted to be coupled to the reamer head 200. In some examples, the handle 400 can form a portion of the reamer head 200.

The handle 400 can include an outer shaft 406 and an inner shaft 408. The outer shaft 406 can be adapted to be coupled to a driver at a proximal end portion (410, FIG. 4B) and to a reamer head 200 at the distal end portion (412, FIG. 4B). The outer shaft 406 can transfer rotational motion from the driver (e.g., a universal driver) to the reamer head 200 to perform a reaming operation. The outer shaft 406 can serve as a housing to the inner shaft 408. The outer shaft 406 can be integral with the housing 202 of the reamer head 200, or form a portion of the housing 202 of the reamer head 200 (FIGS. 2A-2C).

The inner shaft 408 can be disposed inside the outer shaft 406 and coupled to the outer shaft 406 at a clocking mechanism 414. The inner shaft 408 can be coaxial with the outer shaft 406. An actuator 402 can be coupled to the inner shaft 408 at an inner shaft distal end portion 416. In some other examples, the actuator 402 can be included as part of the reamer head 200 (FIGS. 2A-2C), and the distal end 416 of the inner shaft 408 is couplable to the actuator 402 disposed on or in the reamer head 200 rather than being coupled to the inner shaft as shown in the example.

To aid the surgeon in adjusting the cutting size of the reamer head 200, the inner shaft 408 can be clocked to the outer shaft 406 by the clocking mechanism 414. The clocking mechanism 414 can include an indicator 418 that can indicate which cutting size the reamer head 200 is set to cut (e.g., first size, second size, third size). By rotating the outer shaft 406 relative to the inner shaft 408, different sized cutting elements 304, 306, 308 (FIG. 3A-3D) can be extended by displacement elements 404 on the actuator. The displacement elements 404 are described in further detail in FIGS. 5A-5C and 6A, 6B.

In some examples, a grasping surface 420 surrounding the outer shaft 406 can be adapted to be grasped by a surgeon to align the reamer head 200 and apply pressure to a bone site to be reamed. The grasping surface 420 allows the outer shaft 406 (e.g., and inner shaft 408) to transmit rotation to the reaming head 200 (FIG. 2A), while the grasping surface 420 can remain relatively stationary in the hand of the surgeon.

In some examples, the handle 400 shown in FIGS. 1, 4A, 4B can be provided in a different form, or can be omitted. For example, the example reamer heads described herein can be coupled to and be operated by surgical robots, rather than being operated by a handle 400 held by a surgeon. The handle 400 can simply be an extension between a driver and a reamer head to carry the reamer head. In addition, in some examples, features of the handle 400 can be omitted or incorporated directly into the reamer head 200.

Figure 5A:
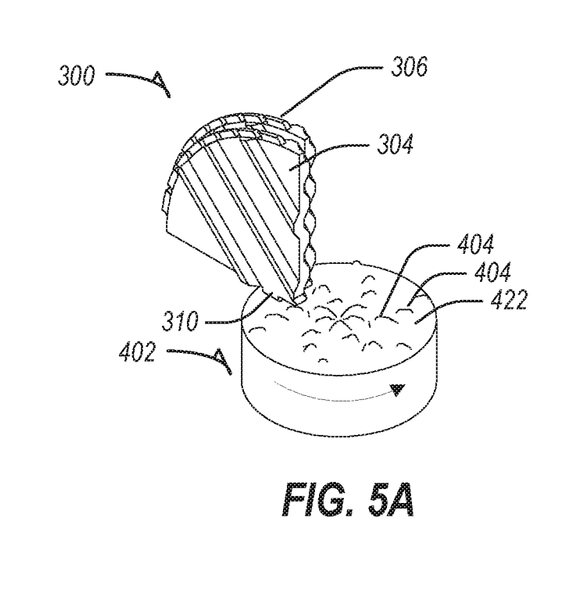
FIG. 5A is a perspective view showing two of the illustrative cutting elements of FIG. 3A and the illustrative actuator of FIG. 4A, in accordance with at least one example.
Figure 5B:
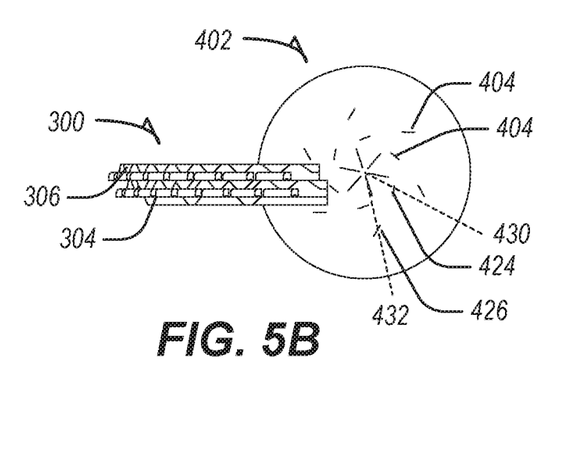
FIG. 5B is a top view of the cutting elements and the actuator of FIG. 5A, in accordance with at least one example.
Figure 5C:
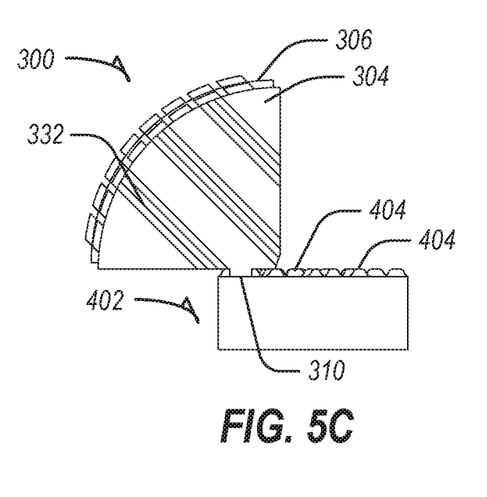
FIG. 5C is a side view of the cutting elements and the actuator of FIG. 5A, in accordance with at least one example.

FIGS. 5A-5C show perspective, top and side views illustrating the first and second cutting elements 304, 306 of FIG. 3A and the illustrative actuator 402 of FIG. 4A, in accordance with at least one example. FIGS. 5A and 5B help illustrate how the first and second cutting elements 304, 306 and the actuator 402 can interact with each other to actuate one of the first and second cutting elements 304, 306.

The actuator 402 can be rotatable to different rotation positions to actuate different cutting elements 300. For example, as shown in FIG. 5A, the second cutting element 306 is actuated into a cutting position (e.g., in an extended position), while the first cutting element is retracted such that it is in a non-cutting position (e.g., FIG. 5C).

The actuator 402 can include a planar disc shaped actuator surface 422 (FIG. 5A) including a plurality of displacement elements 404 (hereinafter displacement elements). The displacement elements 404 can include raised portions extending away from the actuator surface 422. As the actuator 402 is rotated, the displacement elements 404 also rotate. To change which cutting element 300 is actuated, the actuator 402 can be rotated to change the position of the displacement elements 404.

Individual displacement elements (e.g., one of 404) can be positioned to actuate a specified cutting element (e.g., 306, FIG. 5A or 5C). The actuation can be caused by an interaction between a corresponding displacement element (e.g., one of 404) and the actuation interface 310 (also see actuation interface 310 in FIGS. 2C and 3B) of the specified cutting element (e.g., 306, FIGS. 5A and 5B).

The specified cutting element (e.g., 306) can remain in a retracted position when the specified cutting element (e.g., 306) is not lifted and extended by the corresponding displacement element (e.g., one of 404).

For example, the actuator 402 can include a first displacement element 424 and a second displacement element 426 (FIG. 5B). The first displacement element 424 can be configured to displace the first cutting element 304, and the second displacement element 426 can be configured to displace the second cutting element 306.

When the actuator 402 is rotated to a first rotation position 430, the first displacement element 424 on the actuator 402 is caused to displace the first cutting element 304 for cutting. As the first cutting element 304 is lifted by the first displacement element 424, the first cutting element 304 slides into a cutting position along the direction of the alignment elements 332 (FIG. 5C, FIG. 3B).

When the actuator 402 is rotated to a second rotation position 432, the second displacement element 426 on the actuator 402 is caused to displace the second cutting element 306 for cutting. As the second cutting element 306 is lifted by the second displacement element 426, the second cutting element 306 slides into a cutting position along the direction of the alignment elements 332 (FIG. 3B, FIG. 5C). As the second cutting element 306 is lifted, the first cutting element 304 can return to a non-cutting position.

In another arrangement, as each successive cutting element (e.g., 304, 306 etc.) is extended, the cutting elements that have been extended, can remain extended in a cutting position, since an incrementally larger size would stand proud as an effecting cutting diameter of the reamer. In other words, once the cutting element (304, 306, etc.) is extended, it may not necessarily be retracted.

Figure 6A:
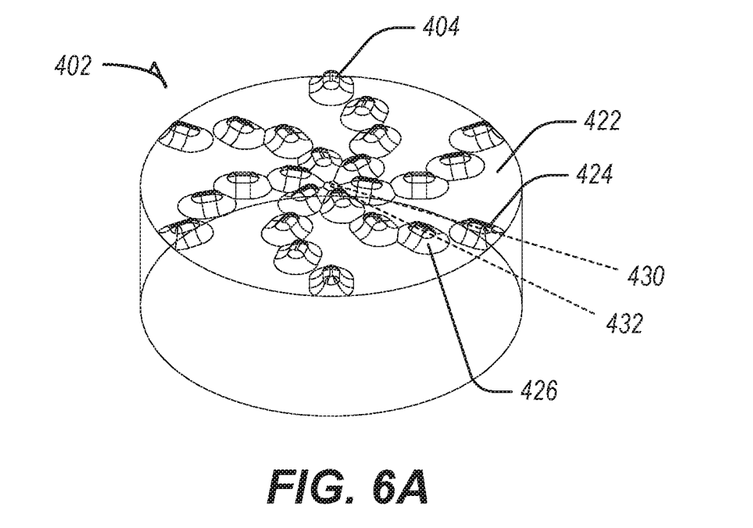
FIG. 6A is detailed perspective view of an actuator that can be used in FIGS. 5A-5B, in accordance with at least one example.
Figure 6B:
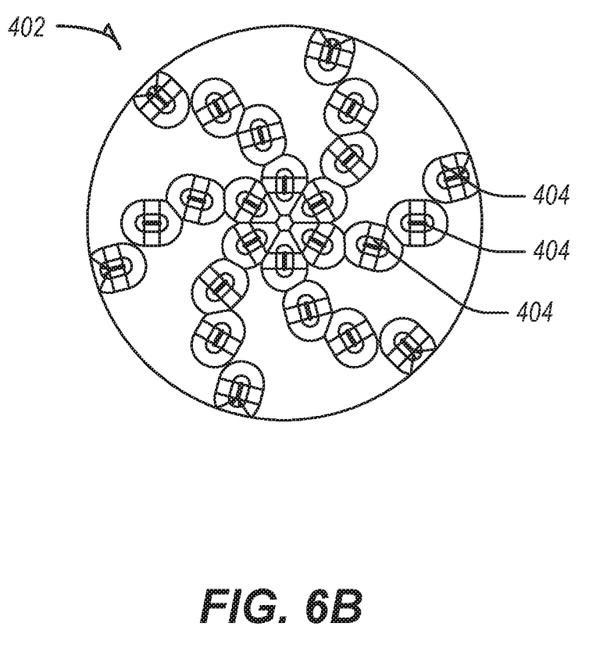
FIG. 6B is a detailed top view of the actuator of FIG. 6A, in accordance with at least one example.

FIGS. 6A and 6B show a detailed perspective view and a detailed top view of an illustrative actuator 402. FIGS. 6A and 6B show how the displacement elements 404 of FIGS. 4A, 4B and 5A-5C can be shaped and arranged to actuate different cutting elements 304, 306 at different rotation positions 430, 432 (FIG. 5B).

As shown in FIGS. 6A and 6B, the spiral starburst arrangement of the displacement elements 404 can provide actuation of a plurality of first cutting elements (FIGS. 3E and 3F) at the first rotation position 430. Then, as the actuator 402 is further rotated into a second rotation position 432, a plurality of second cutting elements 306 can be lifted and actuated (FIG. 3G, 3H). When the plurality of second cutting elements 306 are moved into the cutting position, the plurality of first cutting elements 304, no longer being actuated by the first displacement element 424, can be allowed to retract and rest on the actuator surface 422.

Figure 7:
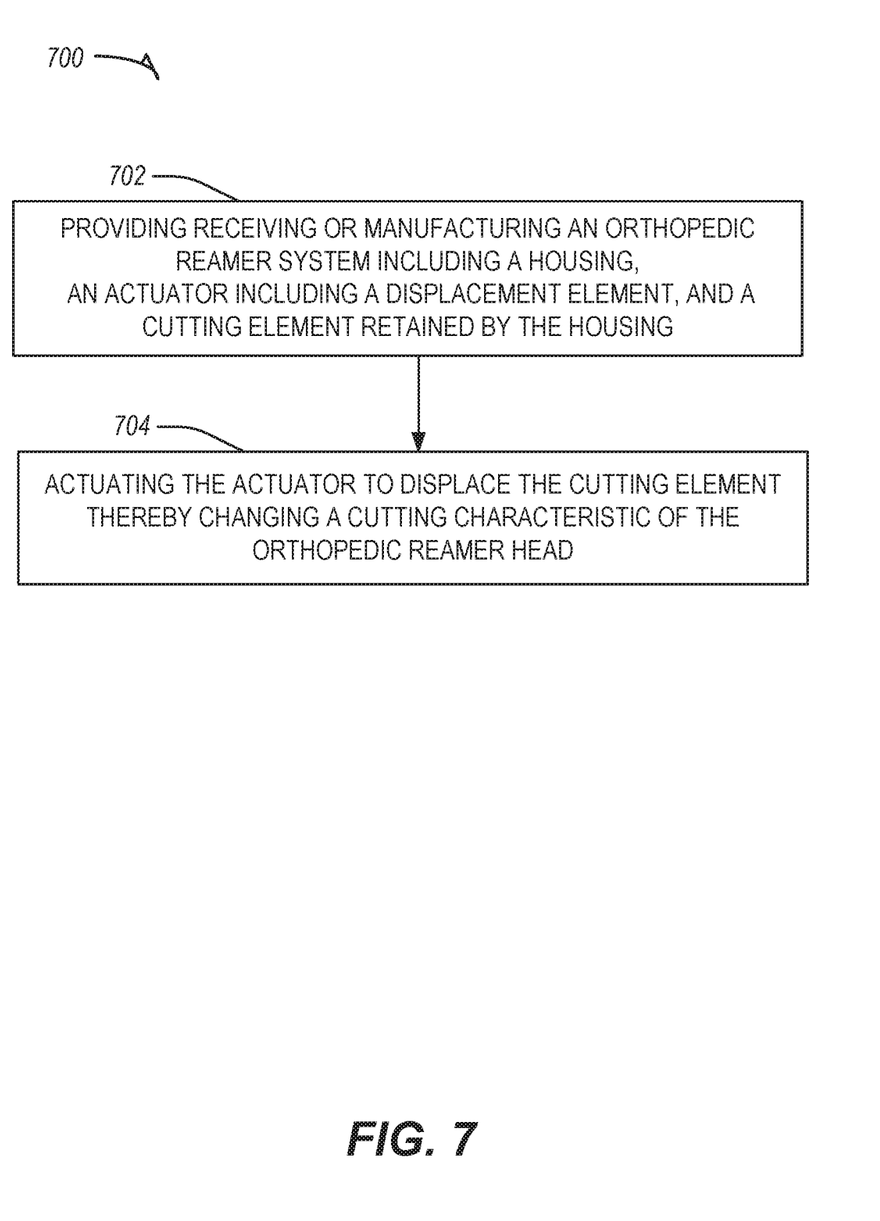
FIG. 7 is an illustrative method of adjusting a cutting characteristic of the orthopedic reamer system of FIG. 1, in accordance with at least one example.

FIG. 7 shows an illustrative technique 700 of adjusting a cutting characteristic of the reamer system of FIG. 1. The technique 700 can be used with the reamer systems 100 described herein, but can also be used with other reamer systems. Alternatively, the reamer systems 100 described herein can also be used with other techniques.

Operation 702 of the technique 700 can include providing, receiving or manufacturing an orthopedic reamer system as described in FIGS. 1, 2A-2C, 3A-3J, 4A, 4B, 5A-5C, 6A and 6B. In some examples, the technique can include providing receiving or manufacturing an orthopedic reamer system including a displacement element and a cutting element retained by a housing.

Operation 704 of the technique 700 can include actuating the actuator to displace the cutting element, thereby changing a cutting characteristic of the orthopedic reamer head. In some examples, actuating the actuator can cause a plurality of a first cutting element to be moved into a cutting position. Further actuating the actuator into a second rotation position can cause a plurality of a second cutting element to be moved into a cutting position.

In operation 704, changing the cutting characteristic can include changing a cutting size, shape, roughness or depth of the orthopedic reamer system.

In operation 704, actuating the actuator can include rotating the actuator relative to the housing to rotate displacement elements thereby extending a cutting element.

The above detailed description includes references to the accompanying drawings, which form a part of the detailed description. The drawings show, by way of illustration, specific examples in which the invention can be practiced. These examples are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other examples can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed example. Thus, the following claims are hereby incorporated into the Detailed Description as examples or examples, with each claim standing on its own as a separate example, and it is contemplated that such examples can be combined with each other in various combinations or permutations. The scope of the invention should be determined with reference to the appended claims, along with the full scope of equivalents to which such claims are entitled.

Numbered Examples

Example 1 is an orthopedic reamer system for preparing a bone to receive an implant, the orthopedic reamer system comprising: a housing; an actuator disposed within a central portion of the housing; and a plurality of cutting elements retained by the housing and operably coupled to the actuator, wherein the plurality of cutting elements include, a first size cutting element and a second size cutting element, and wherein when the actuator is actuated, the first size cutting element and the second size cutting element move relative to one another to change from a first cutting geometry to a second cutting geometry.

In Example 2, the subject matter of Example 1 includes, wherein the first size cutting element includes a first linear alignment element and the second size cutting element includes a second linear alignment element, and wherein the first linear alignment element and the second linear alignment element are nested together to allow the first size cutting element to translate relative to the second size cutting element.

In Example 3, the subject matter of Example 2 includes, wherein the first linear alignment element and the second linear alignment element are formed as grooves or ridges.

In Example 4, the subject matter of Examples 1-3 includes, wherein the actuator is rotatable to different rotation positions, wherein a first rotation position causes the actuator to displace the first size cutting element for cutting, and wherein a second rotation position causes the actuator to displace the second size cutting element for cutting.

In Example 5, the subject matter of Examples 1-4 includes, wherein the actuator includes a first displacement element and a second displacement element, and wherein the first displacement element is configured to displace the first size cutting element and the second displacement element is configured to displace the second size cutting element.

In Example 6, the subject matter of Examples 1-5 includes, wherein the actuator is rotatable to different rotation positions, wherein a first rotation position causes the actuator to displace the first size cutting element to a cutting position, and wherein a second rotation position causes the actuator to withdraw the first size cutting element to a non-cutting position.

In Example 7, the subject matter of Examples 1-6 includes, wherein the actuator is rotatable to a second rotation position, and wherein the second rotation position causes the actuator to displace the second size cutting element to a cutting position and a first rotation position causes the actuator to withdraw the second size cutting element to a non-cutting position.

In Example 8, the subject matter of Examples 1-7 includes, wherein the actuator includes a generally planar disc shaped surface and wherein the first and second displacement elements include raised portions extending away from the generally planar disc shaped surface.

In Example 9, the subject matter of Examples 1-8 includes, wherein the actuator is adapted to be coupled to an inner shaft of a reamer handle, and wherein rotation of the reamer handle causes a rotation of the inner shaft and the actuator.

Example 10 is an orthopedic reamer system for preparing a bone to receive an implant, the orthopedic reamer system comprising: a housing; an actuator coupled to the housing; and a cutting element retained by the housing and operably coupled to the actuator, wherein the cutting element is movable with respect to the housing in a direction having a longitudinal component or an axial component to change a cutting characteristic of the orthopedic reamer system.

In Example 11, the subject matter of Example 10 includes, wherein the cutting element has a generally planar form and includes a perimeter having a curved cutting portion.

In Example 12, the subject matter of Examples 10-11 includes, wherein the actuator is rotatably coupled to the housing, and wherein the actuator includes a plurality of displacement elements arranged to longitudinally or axially displace a plurality of the cutting element when the actuator is rotated.

In Example 13, the subject matter of Example 12 includes, wherein the displacement elements include raised portions on a surface of the actuator.

In Example 14, the subject matter of Examples 10-13 includes, wherein the cutting element is a generally planar element comprising an alignment element, and wherein the cutting element is movable relative to the housing along the alignment element to change a cutting size of the orthopedic reamer system.

In Example 15, the subject matter of Example 14 includes, wherein the alignment element is a groove or ridge.

In Example 16, the subject matter of Examples 10-15 includes, wherein the cutting element includes an alignment element and wherein the housing includes an alignment guide, and wherein the alignment element and the alignment guide are nested together to allow the cutting element to translate relative to the housing.

In Example 17, the subject matter of Examples 10-16 includes, wherein the actuator is rotatable to different rotation positions, wherein a first rotation position causes the actuator to displace the cutting element to a cutting position, and wherein a second rotation position causes the actuator to withdraw the cutting element to a non-cutting position.

In Example 18, the subject matter of Examples 10-17 includes, wherein the actuator is adapted to be coupled to an inner shaft disposed inside of an outer shaft, and wherein rotation of the outer shaft causes a rotation of the inner shaft and the actuator.

In Example 19, the subject matter of Examples 10-18 includes, wherein changing the cutting characteristic includes changing a size, shape, depth or abrasiveness.

Example 20 is a method of changing a cutting characteristic of an orthopedic reamer system for reaming a bone, the method comprising: providing, receiving or manufacturing an orthopedic reamer head having a housing, an actuator including a displacement element, and a cutting element retained by the housing; actuating the actuator to displace the cutting element in a direction having a longitudinal component or an axial component, thereby changing a cutting characteristic of the orthopedic reamer system.

In Example 21, the subject matter of Example 20 includes, wherein changing the cutting characteristic includes changing a cutting size or a depth of the orthopedic reamer system.

In Example 22, the subject matter of Examples 20-21 includes, wherein actuating the actuator includes rotating the actuator relative to the housing.

Example 23 is an orthopedic reamer head for preparing a bone to receive an implant, the orthopedic reamer head comprising: a housing that is couplable to a handle having a cutting element actuator; and a cutting element retained by the housing and operably couplable to the cutting element actuator, wherein the cutting element is movable with respect to the housing in a direction having a longitudinal component or an axial component to change a cutting characteristic of the orthopedic reamer head upon rotation of the cutting element actuator.

In Example 24, the subject matter of Example 23 includes, wherein the cutting element has a generally planar form including a raised linear alignment element and includes a perimeter having a curved cutting portion.

Example 25 is an orthopedic reamer handle for coupling a reamer head to a driver, the reamer handle comprising: an outer shaft couplable to a driver at a proximal end portion and a housing of a reamer head at a distal end portion to transfer rotation motion from a driver to the reamer head; an inner shaft coupled to a cutting element actuator at a distal end portion, the cutting element actuator including a plurality of displacement elements to actuate a plurality of cutting elements on the reamer head; a clocking element to rotate the inner shaft relative to the outer shaft, whereby moving the inner shaft relative to the outer shaft causes at least one of the plurality of displacement elements on the cutting element actuator to move the at least one of the plurality of cutting elements from a retracted position to an extended position, and wherein in the extended position is a cutting position.

Example 26 is at least one machine-readable medium including instructions that, when executed by processing circuitry, cause the processing circuitry to perform operations to implement of any of Examples 1-25.

Example 27 is an apparatus comprising means to implement of any of Examples 1-25.

Example 28 is a system to implement of any of Examples 1-25.

Example 29 is a method to implement of any of Examples 1-25.

What is claimed is:

1. An orthopedic reamer system for preparing a bone to receive an implant, the orthopedic reamer system comprising:
a housing;
an actuator disposed within a central portion of the housing; and
a plurality of cutting elements retained by the housing and operably coupled to the actuator, wherein the plurality of cutting elements include a first size cutting element and a second size cutting element, and wherein when the actuator is actuated, the first size cutting element and the second size cutting element move relative to one another to change from a first cutting geometry to a second cutting geometry, and wherein, when having the first cutting geometry, only one of the first size cutting element and the second size cutting element are in a cutting position.

2. The orthopedic reamer system of claim 1, wherein the first size cutting element includes a first linear alignment element and the second size cutting element includes a second linear alignment element, and wherein the first linear alignment element and the second linear alignment element are nested together to allow the first size cutting element to translate relative to the second size cutting element.

3. The orthopedic reamer system of claim 2, wherein the first linear alignment element and the second linear alignment element are formed as grooves or ridges.

4. The orthopedic reamer system of claim 1, wherein the actuator is rotatable to different rotation positions, wherein a first rotation position causes the actuator to displace the first size cutting element for cutting, and wherein a second rotation position causes the actuator to displace the second size cutting element for cutting.

5. The orthopedic reamer system of claim 1, wherein the actuator includes a first displacement element and a second displacement element, and wherein the first displacement element is configured to displace the first size cutting element and the second displacement element is configured to displace the second size cutting element.

6. The orthopedic reamer system of claim 1, wherein the actuator is rotatable to different rotation positions, wherein a first rotation position causes the actuator to displace the first size cutting element to a cutting position, and wherein a second rotation position causes the actuator to withdraw the first size cutting element to a non-cutting position.

7. The orthopedic reamer system of claim 1, wherein the actuator is rotatable to a second rotation position, and wherein the second rotation position causes the actuator to displace the second size cutting element to a cutting position and a first rotation position causes the actuator to withdraw the second size cutting element to a non-cutting position.

8. The orthopedic reamer system of claim 1, wherein the actuator includes a generally planar disc shaped surface including a first displacement element and a second displacement element, wherein the first and second displacement elements-include raised portions extending away from the generally planar disc shaped surface.

9. The orthopedic reamer system of claim 1, wherein the actuator is adapted to be coupled to an inner shaft of a reamer handle, and wherein rotation of the reamer handle causes a rotation of the inner shaft and the actuator.

10. The orthopedic reamer of claim 1, wherein, when having the second cutting geometry, only the other one of the first size cutting element and the second size cutting element are in the cutting position.

11. The orthopedic reamer of claim 1, further including:
a plurality of cutting element sets, wherein each cutting element set of the plurality of cutting element sets includes the plurality of cutting elements.

12. An orthopedic reamer system for preparing a bone to receive an implant, the orthopedic reamer system comprising:
a housing;
an actuator coupled to the housing, the actuator having a generally planar disc shaped surface and a raised portion of a displacement element extending away from the generally planar disc shaped surface; and
a cutting element retained by the housing and operably coupled to the actuator, wherein, when the actuator is actuated, the displacement element engages the cutting element to move the cutting element with respect to the housing in a direction having a longitudinal component or an axial component to change a cutting characteristic of the orthopedic reamer system.

13. The orthopedic reamer system of claim 12, wherein the cutting element has a generally planar form and includes a perimeter having a curved cutting portion.

14. The orthopedic reamer system of claim 12, wherein the actuator is rotatably coupled to the housing, and wherein the actuator includes a plurality of displacement elements arranged to longitudinally or axially displace the cutting element when the actuator is rotated.

15. The orthopedic reamer system of claim 12, wherein the cutting element is a generally planar element comprising an alignment element, and wherein the cutting element is movable relative to the housing along the alignment element to change a cutting size of the orthopedic reamer system.

16. The orthopedic reamer system of claim 15, wherein the alignment element is a groove or ridge.

17. The orthopedic reamer system of claim 12, wherein the cutting element includes an alignment element and wherein the housing includes an alignment guide, and wherein the alignment element and the alignment guide are nested together to allow the cutting element to translate relative to the housing.

18. The orthopedic reamer system of claim 12, wherein the actuator is rotatable to different rotation positions, wherein a first rotation position causes the actuator to displace the cutting element to a cutting position, and wherein a second rotation position causes the actuator to withdraw the cutting element to a non-cutting position.

19. The orthopedic reamer system of claim 12, wherein the actuator is adapted to be coupled to an inner shaft disposed inside of an outer shaft, and wherein rotation of the outer shaft causes a rotation of the inner shaft and the actuator.

20. The orthopedic reamer system of claim 12, wherein changing the cutting characteristic includes changing a size, shape, depth or abrasiveness.

21. An orthopedic reamer head for preparing a bone to receive an implant, the orthopedic reamer head comprising:
a housing that is couplable to a handle having a cutting element actuator; and
a cutting element retained by the housing and operably couplable to the cutting element actuator, wherein the cutting element is movable with respect to the housing in a direction having a longitudinal component or an axial component to change a cutting characteristic of the orthopedic reamer head upon rotation of the cutting element actuator, and wherein the cutting element has a generally planar form including a raised linear alignment element and a perimeter having a curved cutting portion when viewing the cutting element along a plane parallel to a longitudinal axis of the orthopedic reamer.

22. An orthopedic reamer handle for coupling a reamer head to a driver, the reamer handle comprising:
an outer shaft couplable to a driver at a proximal end portion and a housing of a reamer head at a distal end portion to transfer rotation motion from a driver to the reamer head; and
an inner shaft coupled to a cutting element actuator at a distal end portion, the cutting element actuator having a generally planar disc shaped surface and a plurality of displacement elements, the displacement elements having a raised portion extending away from the generally planar disc to actuate a plurality of cutting elements on the reamer head,
wherein moving the inner shaft relative to the outer shaft causes at least one of the plurality of displacement elements on the cutting element actuator to move at least one of the plurality of cutting elements from a retracted position to an extended position, and wherein in the extended position is a cutting position.

23. A method of changing a cutting characteristic of an orthopedic reamer system for reaming a bone, the method comprising:
providing, receiving or manufacturing an orthopedic reamer head having a housing, an actuator having a generally planar disc shaped surface and a raised portion of a displacement element extending away from the generally planar disc shaped surface, and a cutting element retained by the housing;
actuating the actuator such that the displacement element engages the cutting element to displace the cutting element in a direction having a longitudinal component or an axial component, thereby changing a cutting characteristic of the orthopedic reamer system.

24. The method of changing a cutting characteristic of an orthopedic reamer system of claim 23, wherein changing the cutting characteristic includes changing a cutting size or a depth of the orthopedic reamer system.

25. The method of changing a cutting characteristic of an orthopedic reamer system of claim 23, wherein actuating the actuator includes rotating the actuator relative to the housing.

\* \* \* \* \*

UNITED STATES PATENT AND TRADEMARK OFFICE
CERTIFICATE OF CORRECTION

| | | |
|---|---|---|
| PATENT NO. | : 11,284,908 B2 | |
| APPLICATION NO. | : 16/746038 | |
| DATED | : March 29, 2022 | |
| INVENTOR(S) | : Steven Conrad | |

It is certified that error appears in the above-identified patent and that said Letters Patent is hereby corrected as shown below:

In the Claims

In Column 13, Line 14, in Claim 8, delete "elements-include" and insert --elements include-- therefor In Column 13, Line 20, in Claim 10, after "reamer", insert --system--

In Column 13, Line 24, in Claim 11, after "reamer", insert --system--

Signed and Sealed this
Fifth Day of July, 2022

*Katherine Kelly Vidal*

Katherine Kelly Vidal
*Director of the United States Patent and Trademark Office*